United States Patent [19]

Brussee et al.

[11] Patent Number: 5,329,023

[45] Date of Patent: Jul. 12, 1994

[54] METHOD OF PREPARING OPTICALLY ACTIVE ALCOHOLS WHICH CONSIST SUBSTANTIALLY OR ENTIRELY OF ONE ENANTIOMER

[75] Inventors: Johannes Brussee; Arne Van Der Gen, both of Weesp, Netherlands

[73] Assignee: Duphar International Research B.V., Weesp, Netherlands

[21] Appl. No.: 899,026

[22] Filed: Jun. 15, 1992

Related U.S. Application Data

[63] Continuation of Ser. No. 560,233, Jul. 25, 1990, abandoned, which is a continuation of Ser. No. 287,031, Dec. 21, 1988, abandoned.

[30] Foreign Application Priority Data

Dec. 24, 1987 [NL] Netherlands ............... 8703131

[51] Int. Cl.$^5$ ........................................... C07C 209/48
[52] U.S. Cl. ........................... 549/443; 549/214; 549/442; 549/491; 556/416; 556/417; 556/436; 558/410; 558/430; 558/447; 558/451; 564/356; 564/493; 568/309; 568/322
[58] Field of Search ............ 558/351, 451, 410, 430, 558/447; 549/443, 491, 442, 214; 556/416, 417, 436; 564/356, 493; 568/322, 309

[56] References Cited

U.S. PATENT DOCUMENTS

| | | | |
|---|---|---|---|
| 4,611,076 | 9/1986 | Dong et al. | 558/351 |
| 4,611,077 | 9/1986 | Dong et al. | 558/351 |
| 4,859,784 | 8/1989 | Effenberger et al. | 558/351 X |

FOREIGN PATENT DOCUMENTS

| | | | |
|---|---|---|---|
| 80827 | of 0000 | European Pat. Off. | |
| 0136016 | 4/1985 | European Pat. Off. | |
| 0326063 | 8/1989 | European Pat. Off. | 435/128 |
| 3701383 | 7/1988 | Fed. Rep. of Germany | |
| 2208299 | 9/1987 | Japan | 435/128 |
| 3219395 | 9/1988 | Japan | 435/128 |

OTHER PUBLICATIONS

Synthesis, Communications, Apr. 1981, pp. 270–272; Amouroux et al.
Bull. Chem. Soc., Japan, 59, (1986) pp. 893–895; Kobayashi, et al.
J. Org. Chem. 48, (1983), pp. 2294–2295; Elliott, et al.
Angew. Chem. 99, (1987), pp. 491–492; Effenberger, et al.
Tetrahedron Letters, 24, (1983), pp. 4075–4078; Krepski, et al.
Chemische Berichte, 64 (1931), pp. 427–434; Smith, et al.
Synthesis, (1986), 301–303; Krepski, et al.
Angew. Chem. 77 (1965), No. 24, p. 1139; Becker, et al.
Angew Chem. 99 (1987) pp. 503, 511 and 513 (3 pages presented) Hoffmann.

*Primary Examiner*—Joseph Paul Brust
*Attorney, Agent, or Firm*—Stevens, Davis, Miller & Mosher

[57] ABSTRACT

The invention relates to a method of preparing optically active alcohols which consist substantially (at least 75% e.e.) or entirely of one enantiomer of formula 4

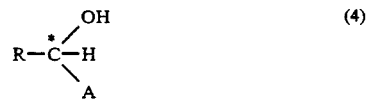

wherein R and A are as defined therein. The method comprises, which maintaining enantiomeric excess, converting an optically active cyanohydrin of formula 1

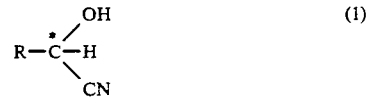

into optically active protected cyanohydrin of formula 2

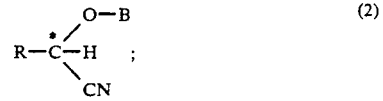

converting the protected cyanohydrin of formula 2 into an optically active compound of formula 3

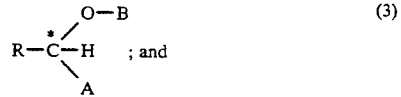

removing the protecting group B.

7 Claims, No Drawings

METHOD OF PREPARING OPTICALLY ACTIVE ALCOHOLS WHICH CONSIST SUBSTANTIALLY OR ENTIRELY OF ONE ENANTIOMER

This application is a continuation of application Ser. No. 07/560,233, filed Jul. 25, 1990, now abandoned, which in turn is a continuation of application Ser. No. 07/287,031, filed Dec. 21, 1988, now abandoned.

The present invention relates to a method of preparing optically active cyanohydrin derivatives and their conversion products and to the optically active compounds to be obtained in this manner.

In the preparation of existing and new products having a biological activity, for example medicines, which comprise a compound having at least one chiral centre as an active component, it is deemed more and more desirable that the active substance is used not as a (racemic) mixture but in the form of a single enantiomer so as to reduce the side effects and to burden the body less heavily with alien components.

Cyanohydrins form an important group of compounds which are suitable as starting products and intermediate products for the preparation of a large number of biologically active compounds (Angew. Chemie 99, 1987, 491–492).

Known methods of preparing optically active cyanohydrins in which one of the enantiomers is formed in excess (enantiomeric excess; e.e.) use 1) dipeptide catalysts (Bull. Chem. Soc. Japan, 59, 1986, 2893–2895; European Patent Application publication no. 0132392), or 2) catalysts comprising a titanate of an optically active tartaric acid derivative, or 3) the enzymatic ester splitting of O-acylated cyanohydrins (European Patent Application publication no. 0080827). 4) Further a 4-steps method is known, which is based on chiral induction by converting the carbonyl group into a chiral acetal (J. Org. Chem. 48, (1983), 2294), and then cleaving this acetal with silylated HCN to obtain a chiral cyanohydrin. 5) The method which up till now has given the highest e.e. in general, is the enantioselective addition of HCN to an aldehyde catalysed by the enzyme mandelonitrile benzaldehyde lyase (R-oxynitrilase E.C. 4.1.2.10). In this manner a few cyanohydrins have been prepared in a high e.e. (Angew. Chemie 99, 1987, 491–492; German patent application 1,300,111 and European patent application no. 0276375).

Furthermore there are some indications that the cyano group in optically active cyanohydrin enantiomers can be converted under acidic conditions into the carboxyl group or an ester group, while maintaining the chirality (Chemische Berichte 64, 1931, 427). However, reactions of chiral cyanohydrins with Grignard reagents or other organometallic compounds which occur in basic conditions, are involved with loss of optical activity, initiated by attack at the hydroxyl group of the cyanohydrin. This causes inter alia racemisation of the reaction product and bad chemical yields (Tetrahedron Letters 24, 1983, 4075 and Synthesis 1981, 270).

It has now been found that optically active cyanohydrins can be converted under both acidic and basic conditions while the optical purity is maintained. The term "optically active" is to be understood to mean a product which consists substantially or entirely of one enantiomer, i.e. at least 75% e.e. More in particular it has been found that optically active alcohols of formula 4

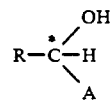

(4)

wherein
R is a monocyclic or bicyclic aryl or heteroaryl group substituted with one or more groups X, wherein X is a hydroxy, alkoxy(1–5 C), alkyl(1–5 C)carbonyloxy, amino, alkyl(1–5 C)carbonylamino, alkyl(1–5 C)sulphonylamino, nitro, alkyl(1–5 C)sulphonyl, alkyl(-1–5 C)carbonyl, halogen, cyano, alkyl(1–5 C), cycloalkyl(5–12 C), or a cyclic group annelated with the aryl group or heteroaryl group, or wherein R is a saturated or unsaturated straight or branched alkyl group having 1–30 C-atoms which may be substituted with halogen, alkoxy(1–5 C), alkylthio(1–5 C), phenyl or phenoxy optionally substituted with one or more groups X, and
A is a radical obtained by derivatisation of the cyano group,
can be obtained while maintaining enantiomeric excess by a) converting an optically active cyanohydrin of formula 1

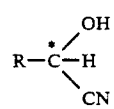

(1)

into an optically active protected cyanohydrin of formula 2

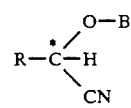

(2)

wherein B is a group protecting the hydroxyl group;

b) converting the protected cyanohydrin of formula 2 into an optically active compound of formula 3

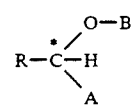

(3)

c) removing the protecting group B.

The protecting group B preferably is a radical of the formula $—Si—R_1R_2R_3$ wherein $R_1$, $R_2$, $R_3$ independently of each other are alkyl or alkenyl(1–8 C), phenyl or aralkyl(1–10 C). Protecting groups B which are to be preferred in particular are the trimethylsilyl group, the tert.butyldimethylsilyl group, the tert.hexyldimethylsilyl group, and the tert.butyldiphenylsilyl group.

Preferred compounds of formulae 3 and 4 are compounds in which A is the group $—CH_2NH_2$, $—CHR_1—NH_2$ or $—CO—R_1$.

The above-mentioned optically active compounds of formulae 2 and 3 are new compounds.

The optically pure compounds of formula 4 to be obtained in this manner may be pharmacologically active compounds or form suitable starting compounds for the preparation of optically pure biologically active products, such as pharmaceuticals, dependent on the meaning of A.

In principle, always one equivalent of base is necessary for the protection reaction of the hydroxyl group (with a group B). It is known, however, (Chemische Berichte 64, 1931, 427) that in these circumstances cyanohydrins show racemisation, or they are converted completely into the corresponding carbonyl compounds. It was found, for example, that optically pure benzaldehyde cyanohydrin in an organic solvent, for example, dimethyl formamide, racemises completely within 24 hours under the influence of an organic base, for example, triethylamine.

It was found surprisingly that the protection reaction (step a) in an organic solvent with a reagent, for example, $R_1R_2R_3$—Si—Hal, can be carried out indeed while maintaining enantiomeric purity in the presence of acid-binding reagents which serve as so-called electrophilic transfer reagents, for example, imidazole.

The compounds having formula 2 with the protected hydroxyl group can now be converted into compounds having formula 3 in a good yield with basic reagents (step b), for example, organometal compounds (analogous to Synthesis, 1986, 301–302). It was found that the enantiomeric excess was maintained in all cases. This is also surprising since a comparatively acid proton is still present in the protected cyanohydrin.

In the case of a Grignard reagent, for example methylmagnesium iodide, optically active product was obtained in a much higher yield than in the analogous reaction with unprotected cyanohydrin. It appeared from NMR-measurements that the e.e. of starting compounds of formula 1 is equal to that of the products of formula 3, thus proving that both the protection reaction (step a), and the cyano derivatisation reaction (step b) occur without racemisation.

From the optically active derived cyanohydrins with protected hydroxyl group with formula 3 to be obtained in the above-described manner the protecting group can be removed selectively while maintaining the optical activity (step c). When B represents a group —Si—$R_1R_2R_3$ methods described in the literature, for example by means of fluoride containing reagents such as tetrabutylammonium fluoride or HF, can be used. In case B is the trimethylsilyl group this step can also be carried out simply by acid hydrolysis of compounds having formula 3.

When a reducing agent is used in step b to convert the cyano group into a primary amine group, for example lithiumaluminium hydride, it has surprisingly been found that the deprotection reaction (step c) occurred immediately after the reduction reaction, so that compounds having formula 4 could be obtained in one step, starting with the corresponding precursors having formula 2. This deprotection reaction of the silyl group by means of lithium aluminium hydride is new, and is caused by the presence of a complexing polar group (in this case an amino group).

Another advantage of the protected cyanohydrins of formula 2 is that they can be purified in a simple manner by means of a physical method of separation, for example distillation or chromatography. Unprotected cyanohydrins are not stable under the conditions necessary for these purification processes. After a deprotection reaction e.g. with HF in an organic solvent both chemically and optically pure cyanohydrins can be obtained.

Another advantage of the method according to the invention is that the preparation of optically pure starting compounds of formula 1 starting from the corresponding aldehyde with HCN in the presence of oxynitrilase can be carried out by means of a crude extract of sweet or bitter almonds. According to the only method known so far (Angew. Chem. 77 (1965), no. 24, p. 1139) the enzyme oxynitrilase to be used in this reaction is first purified after extraction from almonds. It has now been found surprisingly that the crude extract is also suitable for the preparation of optically active cyanohydrins in a good yield. As a result of this, the enzymatic reaction is suitable to be used for the production of optically active cyanohydrins on a large scale.

It was further found that in some cases the optically active cyanohydrins obtained in this manner can be isolated as a pure enantiomer by crystallisation.

The invention will now be described in greater detail with reference to the ensuing specific examples.

EXAMPLE I

Synthesis of R-(+)-α-hydroxy-4-methoxybenzeneacetonitrile a) Enzymatic reaction

Degreased almond meal, 70 g, was mixed with 500 ml of water. The pH was adjusted at 7.4 with 1 N NH$_4$OH. After stirring overnight the mixture was centrifuged (3500 rpm, 5 min.). The supernatant (225 ml) was adjusted at pH 5.4 with 50% acetic acid and transferred to a three-necked flask of 1 l. A solution of 45 g of p-methoxy benzaldehyde (330 mmol) in 160 ml of ethanol was added, in a nitrogen or argon atmosphere, to the enzyme extract and the whole was cooled to 2° C. 400 ml of 1 N KCN/HAc buffer, pH 5.4, were mixed with 160 ml of ethanol, cooled to 2° C. and slowly added dropwise (10 hours) while stirring. After the dropwise addition stirring was continued for another 9 hours at 2° C. The reaction mixture was extracted 4 times with 300 ml of ether. The ether layers were washed three times with 30 ml of saturated NaCl solution, dried on sodium sulphate, filtered and evaporated in a vacuo. Yield of crude product: 52.2 g (96%). NMR: 80 to 85% cyanohydrin and 15 to 20% aldehyde. $[\alpha]^{20}_D = +30.1°$ (c=1, CHCl$_3$).

b) Crystallization

The crude product was dissolved in 110 ml of CH$_2$Cl$_2$ while heating, and 90 ml of petroleum ether (40-60) were slowly added, while heating. Upon cooling slightly, crystallisation set in immediately. After cooling to 4° C. the crystals were filtered and dried. Yield: 35.3 g (65.5% based on starting aldehyde and 77% based on 85% converted aldehyde). Melting-point: 79°–81° C. $[\alpha]^{20}_D = +48°$ (c=1, CHCl$_3$). Another recrystalisation showed no increase of the $[\alpha]^{20}_D$. Enantiomeric purity >95% (NMR). The enantiomeric purity was determined with NMR (200 MHz) after addition of tris-[3-heptafluoropropyl-hydroxymethylene)-d-camphorato]europium III. Racemic product gave two equal signals of the benzylic proton. Optically active product gave one signal of the benzylic proton.

In a similar manner the following compounds have been prepared:

(1) R-(+)-α-hydroxybenzeneacetonitrile: yield (crude product) 98%, $[\alpha]^{20}_D = +45°$ (c=1, CHCl$_3$); melting point 28°–29° C., e.e. >99% (NMR), purity 97% (NMR)

(2) R-(+)-(α-hydroxy)-2-(5-methylfuran)acetonitrile: yield (crude product) 75%; $[\alpha]^{20}_D = +45°$ (c=1, CHCl$_3$); e.e.=95% (NMR); purity 60% (NMR)

(3) R-(+)-2-hydroxypentanenitrile): yield (crude product) 86%; $[\alpha]^{20}_D = +24°$ (c=1, CHCl$_3$); e.e.=93% (NMR); purity 98% (NMR); $n^{20}_D = 1.4216$ (4) R-(−)-2-hydroxy-3-(E)-pentenenitrile: yield (crude product) 60%; $[\alpha]^{20}_D = -22°$ (c=1, CHCl$_3$); e.e.=95% (NMR); $n^{20}_D = 1.4469$; purity 94% (NMR)

(5) R-(+)-α-hydroxy-1,2,5,6-tetrahydrobenzeneacetonitrile: yield (crude product) 86%; $[\alpha]^{20}_D = +10°$ (c=1, CHCl$_3$); $n^{20}_D = 1.4857$; e.e.=55% (NMR); purity 98% (NMR)

(6) R-(+)-α-hydroxy-4-(1,2-benzodioxole)acetonitrile: yield (crude product) 61%; $[\alpha]^{20}_D = +22°$ (c=1, CHCl$_3$); e.e.=93% (NMR); purity 50% (NMR)

EXAMPLE II

Silylation

R-(+)-α-(tert.butyldimethylsilyloxy)-4-methoxybenzeneacetonitrile 4.2 g of imidazole (60 mmol) were dissolved in 75 ml of dry dimethyl formamide (DMF) in a 250 ml three-necked flask. 6.9 g of tert.butyldimethylsilyl chloride (TBSCl, 45 mmol) were added, while cooling, in such a manner that the reaction temperature did not exceed 20° C. After stirring for 15 minutes, 4.95 g of p-methoxybenzaldehyde cyanohydrin (30 mmol) were added. After stirring at room temperature for 1 hour the mixture was poured into 150 ml of water and extracted three times with 100 ml of ether. The collected ether layers were washed three times with 30 ml of water, dried on MgSO$_4$, filtered and evaporated. Yield 71% (after flash-chromatography), $[\alpha]^{20}_D = +16°$ (c=1, CHCl$_3$), $n^{20}_D = 1.4923$, purity >99% (NMR). Determination of the e.e. by means of the NMR-method was not possible, due to lack of complexation capacity of the silyl substituted oxygen atom.

The following compounds have been obtained in the same manner:

(1) R-(+)-α-(trimethylsilyloxy)-4-methoxybenzeneacetonitrile; yield (crude product) 96%, $[\alpha]^{20}_D = +22°$ (c=1, CHCl$_3$), $n^{20}_D = 1.4823$, purity 96% (NMR);

(2) R-(+)-α-(hexyldimethylsilyloxy)-4-methoxybenzeneacetonirile; yield 67% (after flash-chromatography), $[\alpha]^{20}_D = +15°$ (c=1, CHCl$_3$), $n^{20}_D = 1.5009$, purity >99% (NMR);

(3) R-(−)-α-(tert.butyldiphenylsilyloxy)-4-methoxybenzeneacetonitrile; yield 73% (after crystallization from petroleumether boiling point 40°-60°), $[\alpha]^{20}_D = -47°$ (c=1, CHCl$_3$), melting point 80°-82° C., purity >99% (NMR);

(4) R-(+)-α-(trimethylsilyloxy)-benzeneacetonitrile; yield 99% (crude product), $[\alpha]^{20}_D = +28°$ (c=1, CHCl$_3$), $n^{20}_D = 1.4860$, purity 95% (NMR);

(5) R-(+)-α-(tert.butyldimethylsilyloxy)-benzeneacetonitrile; yield 79% (after flash-chromatography, $[\alpha]^{20}_D = +17°$ (c=1, CHCl$_3$), $n^{20}_D = 1.4834$, purity >99% (NMR);

(6) R-(−)-α-(tert.butyldiphenylsilyloxy)-benzeneacetonitrile; yield 67% ( after flash-chromatography), $[\alpha]^{20}_D = -15°$ (c=1, CHCl$_3$), $n^{20}_D = 1.5632$, purity >99% (NMR);

(7) R-(+)-α-(tert.butyldimethylsilyloxy)-2-(5-methylfuran)acetonitrile: yield 81% (after crystallization from methanol/water), $[\alpha]^{20}_D = +24°$ (c=1, CHCl$_3$), melting point 40°-41° C., purity >99% (NMR);

(8) R-(+)-2-(tert.butyldimethylsilyloxy)-pentanenitrile; yield 85% (after distillation, boiling point 106°-108° C. at 1 mmHg), $[\alpha]^{20}_D = +48°$ (c=1, CHCl$_3$), $n^{20}_D = 1.4270$, purity >95% (NMR);

(9) R-(+)-2-(tert.butyldimethylsilyloxy)-3-(E)-pentenenitrile; yield 74% (after flash-chromatography), $[\alpha]^{20}_D = +11°$ (c=1, CHCl$_3$), $n^{20}_D = 1.4402$, purity >99% (NMR);

(10) R-(+)-α-(tert.butyldimethylsilyloxy)-1,2,5,6-tetrahydrobenzeneacetonitrile; yield 44% (after flash-chromatography), $[\alpha]^{20}_D = +18°$ (c=1, CHCl$_3$), $n^{20}_D = 1.4637$, purity >95% (NMR);

(11) R-(+)-α-(tert.butyldimethylsilyloxy)-4-(1,2-benzodioxole)acetonitrile; yield 52% (after flash-chromatography), $[\alpha]^{20}_D = +17°$ (c=1, CHCl$_3$), $n^{20}_D = 1.5007$, purity >95% (NMR).

EXAMPLE III

Deprotection of the silyated hydroxyl group

R-(+)-2-hydroxypentanenitrile

20 Mmol of R-(+)-2-(tert.butyldimethylsilyloxy)pentanenitrile were dissolved in 25 ml of acetonitrile, and 2 ml of 40% HF in water (40 mmol) were added. The reaction was carried out at 45° C. After stirring for 5 hours 50 ml of water were added, and the mixture was extracted three times with 25 ml of ether. The ether layers were washed with a saturated NaCl-solution, dried on MgSO$_4$, filtered and evaporated.

Yield 95%, $[\alpha]^{20}_D = +23°$ (c=1, CHCl$_3$), e.e.=94% (NMR), purity >98% (NMR).

The following protected cyanohydrins have been deprotected in the same manner:

1) R-(+)-α-(tert.butyldimethylsilyloxy)-benzeneacetonitrile;

2) R-(+)-α-(tert.butyldimethylsilyloxy)-4-methoxybenzeneacetonitrile;

3) R-(+)-2-(tert.butyldimethylsilyloxy)-3-(E)-pentenenitrile;

4) R-(+)-α-(tert.butyldimethylsilyloxy)-1,2,5,6-tetrahydrobenzeneacetonitrile.

Since no change of optical activity of the cyanohydrins was observed after protection and deprotection it was concluded that both steps occur with maintenance of e.e.

EXAMPLE IV

Silyl protected acyloins

R-(+)-1-(tert.butyldimethylsilyloxy)-1-(4-methoxyphenyl)-2-propanone 9.7 g of R-(+)-α-{(tert.butyldimethylsilyl)oxy}-4-methoxybenzeneacetonitrile (35 mmol) in 100 ml of dry ether were added dropwise to a solution of 11.7 g of methylmagnesium iodide (70 mmol) in 200 ml of ether. After stirring under reflux for four hours the reaction mixture was poured in 420 g of ice and 9 ml of concentrated sulphuric acid. After stirring for a few minutes the layers were separated and the aqueous layer was extracted three times with 100 ml of ether. The collected ether layers were washed with 100 ml of 10% sodium bicarbonate and 100 ml of water, dried on magnesium sulphate, filtered and evaporated.

Yield 80% (after flash-chromatography), $[\alpha]^{20}_D = +60°$ (c=1, CHCl$_3$), $n^{20}_D = 1.4898$, e.e.=99% (NMR), purity >99% (NMR).

The following protected acyloins were prepared in the same manner:

(1) R-(+)-1-(tert.butyldimethylsilyloxy)-1-phenyl-2-propanone; yield 80% (after flash-chromatography), $[\alpha]^{20}_D = 61°$ (c=1, CHCl$_3$), $n^{20}_D = 1.4813$, e.e. =92% (NMR), purity >99% (NMR);

(2) R-(+)-3-(tert.butyldimethylsilyloxy)-2-hexanone; yield 74% (after flash-chromatography), $[\alpha]^{20}_D = +30°$ (c=1, CHCl$_3$), $n^{20}_D = 1.4313$, purity >99% (NMR).

EXAMPLE V

Acyloins

R-(−)-1-hydroxy-1-(4-methoxyphenyl)-2-propanone 1.5 g of R-(+)-α-(trimethylsilyloxy)-4-methoxybenzeneacetonitrile (6.4 mmol, e.e. 75%) in 15 ml of dry ether were added dropwise to a solution of 2.05 g of methyl magnesium iodide (12.3 mmol) in 40 ml of dry ether in a 100 ml round-bottomed flask. The solution was stirred under reflux for 4 hours. The reaction mixture was then poured in 70 g of ice and 3 ml of concentrated sulphuric acid, after which stirring at room temperature was continued for 17 hours. The layers were separated and the water layer was extracted twice with 40 ml of ether. The collected ether layers were washed with water, dried on magnesium sulphate and evaporated.

Yield 78% (after flash-chromatography), $[\alpha]^{20}_D = -343°$ (c=1, CHCl$_3$), e.e. =96% (NMR), purity >99% (NMR).

The following compound was prepared in the same manner.

R-(−)-1-hydroxy-1-phenyl-2-propanone; yield 71% (after flash-chromatography), $[\alpha]^{20}_D = 393°$ (c=1, CHCl$_3$), and $[\alpha]^{20}_D = 141°$ (c=1, ethanol), $n^{20}_D = 1.5291$, e.e. =95% (NMR), purity >99% (NMR).

EXAMPLE VI

Ethanolamines by reducing with LiAl$_4$

R-(−)-α-(aminoethyl)-4-methoxybenzenemethanol 1.4 g of LiAlH$_4$ (36.8 mmol) in 30 ml of dry THF were provided in a 100 ml three-necked flask comprising a cooler with calcium chloride tube and a counter-pressure dropping funnel. A solution of 6.9 g of R-(+)-α-(tert.butyldimethylsilyloxy)-4-methoxybenzeneacetonitrile (24.9 mmol) in 10 ml of dry THF was slowly added dropwise. After the addition reflux was carried out for 1 hour. After cooling the reaction mixture, 1.4 ml of water, 1.4 ml of 15% NaOH and 4.2 ml of water were added dropwise successively. The precipitate formed was filtered, washed with THF. The filtrate was dried on Na$_2$SO$_4$ and then evaporated. Yield: 4.7 g of solid substance (theoretically: 4.2 g). The crude product was stirred for 30 minutes with 100 ml of petroleum ether 40-60, and filtered.

Yield: 3.8 g of pale yellow crystalline product (90%). $[\alpha]^{20}_D = -33°$ (c=1, abs. EtOH). Recrystallisation from dichloromethane/petroleum ether 40-60 yielded a crystalline product of melting-point 102°-103° C.

$[\alpha]^{20}_D = -39°$ (c=1, abs. EtOH).

The following compounds have been obtained in a similar way:

(1) R-(−)-α-(aminomethyl)-benzenemethanol; $[\alpha]^{20}_D = -42°$ (c=1, ethanol), melting point 54°-58° C., e.e. 95%;

(2) R-(−)-1-amino-2-pentanol; yield 86% (crude product), $[\alpha]^{20}_D = -12°$ (c=1, CHCl$_3$), $[\alpha]^{20}_D = -0.4°$ (c=1, abs. ethanol), $n^{20}_D = 1.4497$, purity 90% (NMR).

EXAMPLE VII

Ethanolamines through Grignard-reduction sequence (1R,2S),(−)-2-amino-1-phenyl-1-(tert.butyldimethylsilyloxy)-propane 6.0 g of R-(+)-α-(tert.butyldimethylsilyloxy)-benzeneacetonitrile (24 mmol) in 100 ml of dry ether were added to a Grignard solution of 8.0 g of CH$_3$MgI (48 mmol) in 70 ml of dry ether, and the mixture was refluxed during 4 hours. A solution of 1.7 g of NaBH$_4$ (45 mmol) in 50 ml of methanol was added dropwise. After stirring for 17 hours at room temperature the formed salts were removed by filtration and the filtrate was washed twice with 100 ml of water. After drying and evaporating the organic layer 6.0 g of a pale yellow oil was obtained.

Yield 94% (crude product), $[\alpha]^{20}_D = -38°$ (c=1, CHCl$_3$), purity >90% (NMR), erythro/threo=90/10 (NMR).

EXAMPLE VIII

Deprotection with LiAlH$_4$ (1R,2S)-(−)-2-amino-1-phenylpropanol.HCl 5.0 g of (1R,2S)-(−)-2-amino-1-phenyl-1-(tert.butyldimethylsilyloxy)-propane (18.8 mmol) in 50 ml of dry THF were added dropwise while refluxing to a solution of 1 g of LiAlH$_4$ (26 mmol) in 50 ml of dry THF. After stirring for 1 hour the mixture was cooled to room temperature, and a solution of 1 ml of water in 10 ml of THF, 1 ml of 15% sodium hydroxide and 3 ml of water respectively were added dropwise. The formed salts were removed by filtration, and the filtrate was dried and evaporated. Yield 99% (crude product).

This product was dissolved in 20 ml of ethanol, and 29.5 ml of 0.48 N HCl in ethanol were added. The mixture was evaporated, and 100 ml of dry ether were added to the residue. The crystalline product was filtered off.

Yield 50%, $[\alpha]^{20}_D = -28°$ (c=1, H$_2$O), melting point 144°-146° C., purity >99%.

I claim:

1. A method of preparing optically active alcohols which consist substantially (at least 75% enantiomeric excess) or entirely of one enantiomer of formula (4)

(4)

wherein R is phenyl, 1,2,5,6-tetrahydrophenyl, furan or benzodioxole, said R groups being substituted with one or more groups X, wherein X is a hydroxy, alkoxy(1-5 C), alkyl(1-5 C)carbonyloxy, amino, alkyl(1-5 C)carbonylamino, alkyl(1-5 C)sulphonyl, nitro, alkyl(1-5 C)suphonylamino, alkyl(1-5 C)carbonyl, halogen, cyano, alkyl(1-5 C)or cycloalkyl(5-12 C),or wherein R is a saturated or unsaturated straight or branched alkyl group having up to 30 C-atoms which may optionally be substituted with halogen, alkoxy(1-5 C), alkylthio(-1-5 C),phenyl or phenoxy which may optionally be substituted with one or more groups X, and A is selected from the group consisting of —CH$_2$NH$_2$, —CHR$_1$—NH$_2$ and —CO—R$_1$, wherein R$_1$ is alkyl (1-8 C), alkenyl(up to 8 C), phenyl or aralkyl(up to 10 C), comprising
a) protecting the hydroxyl group of an optically active cyanohydrin of formula (1)

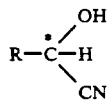 (1)

by reacting with a suitable base giving an optically active protected cyanohydrin of formula (2)

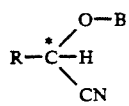 (2)

wherein B is a group protecting the hydroxy group which is a radical of the formula $-Si-R_1R_2R_3$, $R_1$ being as defined above, $R_2$ and $R_3$ independently of each other being alkyl(1–8 C), alkenyl (up to 8 C), phenyl or aralkyl(up to 10 C);
b) reacting the nitrile group of the protected cyanohydrin of formula (2) with a suitable base reagent giving an optically active compound of formula (3)

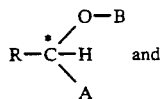 (3)

c) removing the protecting group B.

2. A method as claimed in claim 1, wherein the protecting group B is selected from the group consisting of trimethylsilyl, tert.butyldimethylsilyl, tert.hexyldimethylsilyl and tert.butyldiphenylsilyl.

3. A method as claimed in claim 1, wherein $R_1$ is methyl.

4. A method as claimed in claim 1, wherein reaction step a) is carried out in the presence of an electrophilic transfer reagent.

5. A method as claimed in claim 1, wherein step c) is carried out with lithium aluminum hydride.

6. A method as claimed in claim 2, wherein step c) is carried out with lithium aluminum hydride.

7. A method as claimed in claim 4, wherein the electrophilic transfer reagent is imidazole.

* * * * *